United States Patent [19]

Stedman et al.

[11] Patent Number: 4,883,059
[45] Date of Patent: Nov. 28, 1989

[54] INTRAVAGINAL TRANSDUCER BIOPSY GUIDE

[75] Inventors: David Stedman, Kirkland; Norio Harui, Seattle, both of Wash.

[73] Assignee: Advanced Technology Laboratories, Inc., Bothell, Wash.

[21] Appl. No.: 933,708

[22] Filed: Nov. 21, 1986

[51] Int. Cl.⁴ ............................................. A61B 10/00
[52] U.S. Cl. .................................. 128/660.01; 128/754
[58] Field of Search .................. 128/660, 749, 4, 751, 128/752, 753, 754, 303.19, 74 A; 206/365; 604/197, 198

[56] References Cited

U.S. PATENT DOCUMENTS

| | | | |
|---|---|---|---|
| 2,740,404 | 4/1954 | Kohl | 604/198 |
| 3,356,089 | 12/1967 | Francis | 604/197 |
| 3,380,448 | 4/1968 | Sadove et al. | 206/365 |
| 4,136,695 | 1/1979 | Dafoe | 604/198 |
| 4,469,106 | 9/1984 | Harui | 128/660 |
| 4,573,976 | 3/1986 | Sampson et al. | 604/198 |
| 4,576,175 | 3/1986 | Epstein | 128/660 |
| 4,608,989 | 9/1986 | Drue | 128/660 |
| 4,742,829 | 5/1988 | Law et al. | 128/754 |

Primary Examiner—Edward M. Coven
Assistant Examiner—Timothy G. Philips
Attorney, Agent, or Firm—Christensen, O'Connor, Johnson & Kindness

[57] ABSTRACT

The present invention is a biopsy guide for use with a medical ultrasound scanhead of the type used for intravaginal scans and ultrasound guided biopsies. The guide fits over an intravaginal scanhead, and it includes a slot for guiding a biopsy needle. The guide also includes a unique needle cover which is slidably attached to the guide and which encloses a biopsy needle until actual flesh penetration is desired, thereby preventing unnecessary injury to a patient in the course of the examination.

10 Claims, 3 Drawing Sheets

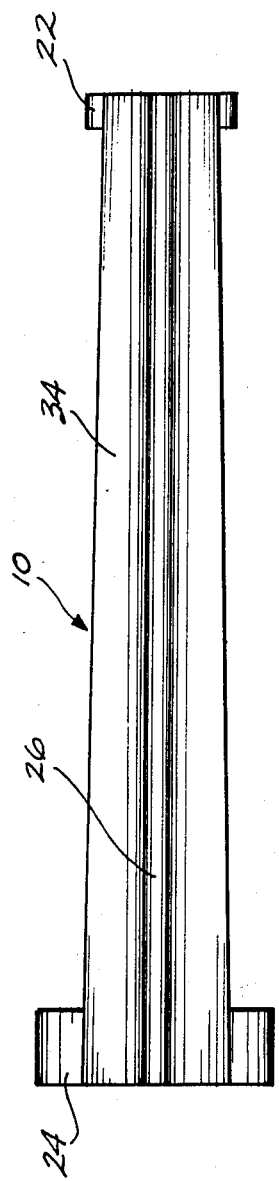
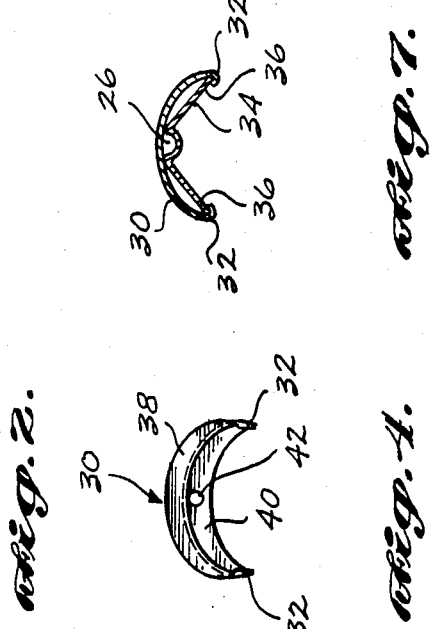
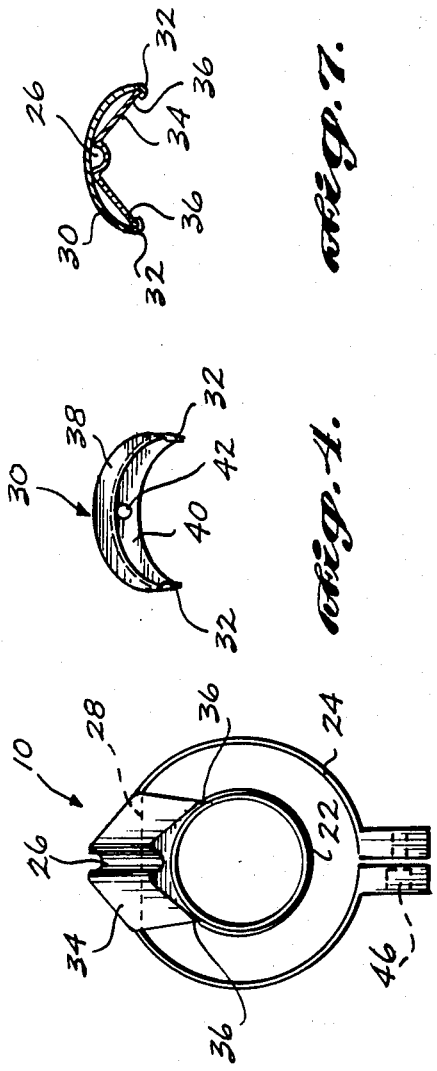

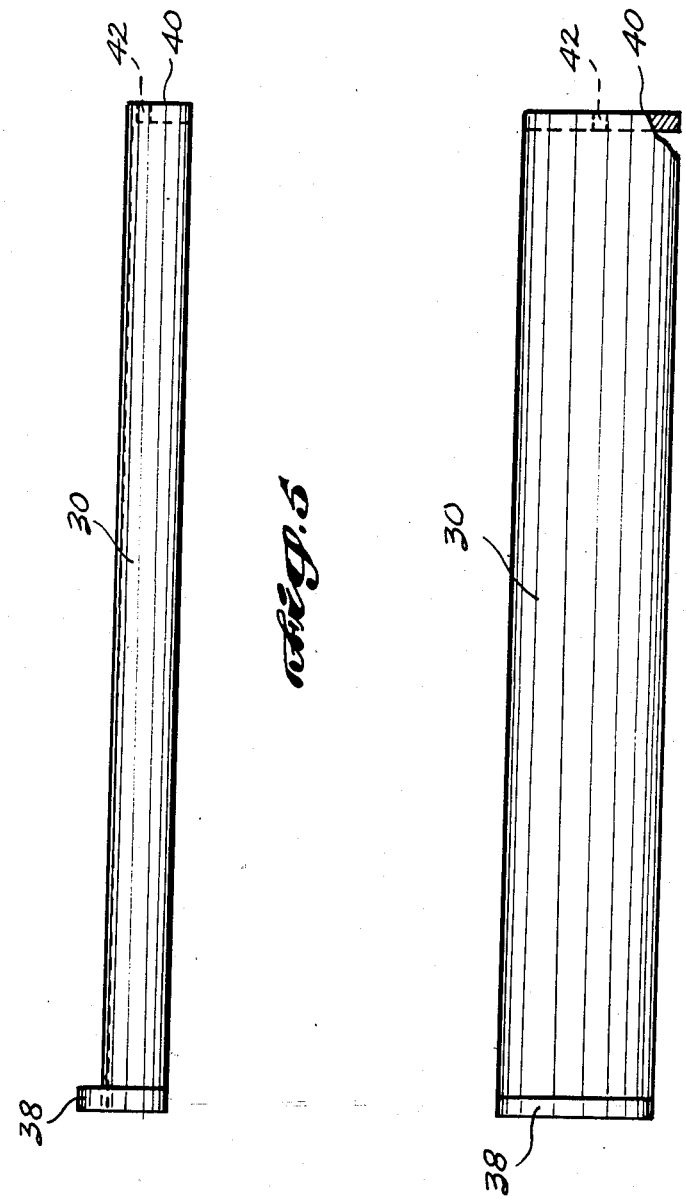

INTRAVAGINAL TRANSDUCER BIOPSY GUIDE

BACKGROUND OF THE INVENTION

The present invention relates to a biopsy guide for use in connection with medical ultrasound equipment. In particular, the invention is a biopsy guide for use with an intravaginal transducer.

Medical ultrasound equipment is used for diagnostic purposes. An intravaginal transducer is a type of medical ultrasound transducer which is used in connection with a diagnostic medical ultrasound scanner to produce images on a cathode ray tube (CRT) display.

It is common in some types of medical ultrasound scanning to identify on the CRT image a region which warrants invasive investigation, i.e., biopsy testing. Accordingly, there have heretofore been developed various needle guides for use in connection with various types of medical ultrasound transducers, the intent of such devices to allow a physician who is looking at an image undergoing ultrasound examination to direct a biopsy needle to a specific site under investigation.

A problem which has heretofore existed in connection with certain types of biopsy procedures, i.e., in intravaginal procedures, has been to prevent the biopsy needle from entering the patient in an undesired area. It is not desirable to have the biopsy needle enter the patient's flesh outside of the area of the ultrasound scan. However, the biopsy guides which have heretofore existed did not prevent such undesirable results.

SUMMARY OF THE INVENTION

The present invention is a biopsy guide for use with a medical ultrasound scanhead of the type used for intravaginal scans and ultrasound guided biopsies.

The guide fits over an intravaginal scanhead, and it includes a slot for directing a biopsy needle. The guide also includes a unique needle cover which is slidably attached to the guide and which encloses a biopsy needle until actual flesh penetration is desired, thereby preventing unnecessary injury to a patient in the course of the examination.

BRIEF DESCRIPTION OF THE DRAWING

In the Drawing:

FIG. 2 is a top view of the biopsy guide of the present invention;

FIG. 3 is an end view of the biopsy guide of the present invention;

FIG. 4 is an end view of the needle guide cover portion of the biopsy guide of the present invention;

FIG. 5 is a side view of the needle guide cover portion of the biopsy guide of the present invention; and FIG. 6 is a top view of the needle guide cover portion of the biopsy guide of the present invention and FIG. 7 is a cross-sectional view of the biopsy guide of the present invention.

DETAILED DESCRIPTION OF AN EXEMPLARY EMBODIMENT

Figure 1:
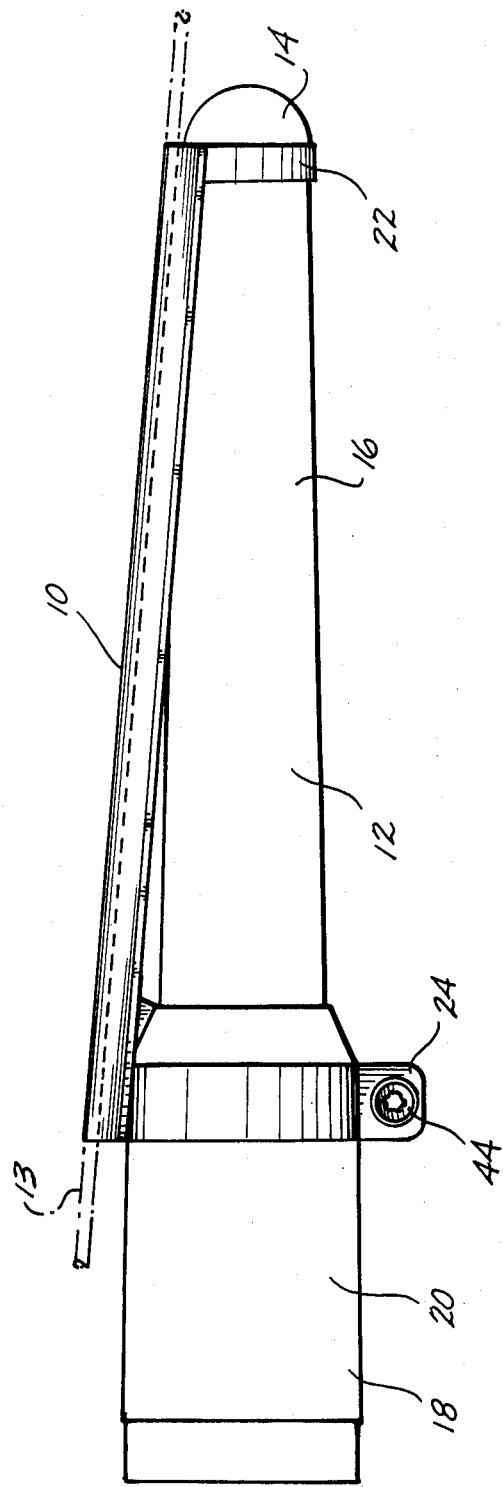
FIG. 1 is a side view of the biopsy guide of the present invention mounted on an intravaginal ultrasound scanhead.

Referring to FIG. 1, the biopsy guide 10 of the present invention is shown mounted on an intravaginal ultrasound scanhead 12, of the type used in conducting scans within a female's vagina. The scanhead 12 is somewhat conical in shape, and it typically includes an ultrasound transducer (not shown) within its distal region 14. In common parlance, the entire scanhead 12 is sometimes referred to as a transducer. The main body 16 of the scanhead 12 is used to position the region 14 containing the transducer in a location from which an appropriate ultrasound examination can be conducted.

At the proximal end 18 of the scanhead 12, there is a housing region 20 in which a motor is typically located for driving the transducer within the distal region 14. A cable (not shown) connects the scanhead 12 to the ultrasound scanner (not shown).

The present invention is the needle guide 10 which is mounted on the scanhead 12. The needle guide 10, shown in greater detail in FIGS. 2-4, includes a front ring 22 and a rear ring 24 which slide over the body of the scanhead 12. The rings 22, 24 include means for keying the needle guide 10 in position on the scanhead 12, such that a needle 13, which is placed into a slot or groove 26 formed on the needle guide 10, will be oriented in the plane of the scan during an ultrasound examination. In the preferred embodiment of the needle guide 10, the means for keying the needle guide 10 in position on the scanhead 12 includes a flat region 28 formed on the inner opening of the rear ring 24 (See FIG. 3). However, other means can be used to accomplish this result.

A particular advantage of the present needle guide 10 over the prior art is that it includes a needle guide cover 30 shown in FIGS. 4-6. The needle guide cover 30 is preferably comprised of an easily sterilizable material. In the preferred embodiment of the invention, the needle guide cover 30 is comprised of a thin sheet of stainless steel which is of a length corresponding to the length of the body of the needle guide 10. The needle guide cover 30 includes means for slidably attaching it to the needle guide 10. In the preferred embodiment of the invention 10, the needle guide cover 30 includes a pair of curved lips 32 which slidably connect the needle guide cover 30 to the elongated ramp portion 34 of the needle guide 10 by wrapping around the rounded shoulders 36 thereof (See FIGS. 3-4 and 7).

The needle guide cover 30 includes a thumb hold 38 at its proximal end for positioning the cover and a needle end plate 40 at its distal end. In the operation of the present invention 10, a biopsy needle is placed into the needle slot 26 and covered by the needle cover 30. The scanhead 12 is inserted into the vagina with the biopsy needle enclosed by the needle cover 30. When a region is imaged from which a biopsy sample is desired, the needle guide cover 30 and biopsy needle are slid down the ramp portion 34 of the biopsy guide 10 until the needle end cover 40 and the needle 13 are visualized. Thus, the needle end cover 40 may be placed into intimate contact with the portion of the patient's flesh which is to be punctured without exposing the needle to the patient until the physician is ready to actually enter the patient's flesh. At that point, the needle is advanced through an opening 42 in the needle end plate 40 and on into the site from which the biopsy is to be performed, all under ultrasound guidance, and all the while without exposing the patient to the needle, until actual penetration is desired.

In the preferred embodiment of the invention, the needle guide 10 is held in position on the scanhead 12 by means of a thumb screw 44 which fits within an opening 46 in the rear ring 24 (See FIG. 3). Tightening the thumb screw 44 serves to bring a pair of flanges 46 on the rear ring 24 together, thereby securing the guide 10 the scanhead 12.

As will be obvious to those of ordinary skill in the art, the present invention can be constructed in a number of ways. While the preferred embodiment utilizes a casted needle guide 10, an a formed stainless steel needle guide cover 30, other suitable approaches can be used to provide the same type of device.

We claim:

1. An improved needle guide, for use in connection with a medical ultrasound scanhead to guide a biopsy needle, of the type comprising:
   (a) a body;
   (b) slot means on said body for directly engaging and guiding the biopsy needle; and
   (c) attachment means for attaching said body to the ultrasound scanhead and providing a desired alignment between said slot means and the ultrasound scanhead,
   the improvement comprising needle cover means which is slidably attached to said body, said needle cover means including means for covering the biopsy needle when the biopsy needle is within said slot means and preventing intimate contact between the needle and a patient until the needle is properly positioned.

2. An apparatus, for use in connection with an ultrasound scanhead to guide a needle, comprising:
   (a) a body defining guide means for directly engaging and guiding the needle;
   (b) attachment means for attaching said body to the ultrasound scanhead; and
   (c) a needle cover means, slidably attachable to said body, for controllably covering the needle when the needle is engaged by said guide means.

3. The apparatus of claim 2, wherein said guide means comprises a groove extending the length of said body and being dimensioned for receiving the needle.

4. The apparatus of claim 3, wherein said body comprises a pair of shoulders for cooperatively engaging said cover means.

5. The apparatus of claim 4, wherein said cover means comprises a pair of lips for cooperatively engaging said shoulders of said body.

6. The apparatus of claim 5, wherein said cover means further comprises a cover plate extending between said pair of lips.

7. The apparatus of claim 6, wherein said cover means has first and second ends and further comprises an end plate, provided at said first end and including an opening that is alignable with said groove in said body to allow the needle to project from said cover means when a desired position of the needle is achieved.

8. The apparatus of claim 7, wherein said cover means further comprises positioning means, provided at said second end of said cover means, for allowing the position of said cover means with respect to said body to be adjusted.

9. The apparatus of claim 8, wherein said attachment means further comprises first and second rings connected to said body for engaging said scanhead.

10. The apparatus of claim 9, wherein one of said rings includes means for providing a desired alignment between said groove in said body and said ultrasound scanhead.

* * * * *